United States Patent [19]

Taylor et al.

[11] Patent Number: 4,524,224

[45] Date of Patent: Jun. 18, 1985

[54] HYDROLYSIS OF ALKYLENE CARBONATES TO AKLYLENE GLYCOLS

[75] Inventors: Glenn A. Taylor, Ridgewood, N.J.; Philip F. Wolf, Pleasantville, N.Y.

[73] Assignee: Union Carbide Corporation, Danbury, Conn.

[21] Appl. No.: 495,462

[22] Filed: May 20, 1983

Related U.S. Application Data

[63] Continuation of Ser. No. 100,223, Dec. 4, 1979, abandoned, which is a continuation of Ser. No. 863,351, Dec. 22, 1977, abandoned.

[51] Int. Cl.³ .................. C07C 29/12; C07C 31/12
[52] U.S. Cl. ................................................. 568/858
[58] Field of Search ...................................... 568/858

[56] References Cited

U.S. PATENT DOCUMENTS 3,629,343 12/1971 Levin et al. ...................... 568/858
4,117,250 9/1978 Foster ............................... 568/858

FOREIGN PATENT DOCUMENTS 267618 7/1970 U.S.S.R. ............................ 568/858

Primary Examiner—J. E. Evans

Attorney, Agent, or Firm—Norman L. Balmer

[57] ABSTRACT

This invention is concerned with producing glycols of the formula

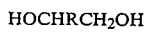

from hydrolysis, in a homogeneous liquid phase mixture, of an alkylene carbonate of the formula

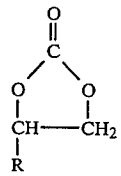

in which R is either hydrogen or methyl. This is accomplished by using an amount of water in excess of stoichiometry and using potassium carbonate as the preferred catalyst. The reaction is effected under a carbon dioxide pressure of at least 80 psig and the reaction temperature is desirably between about 85° C. and 500° C.

17 Claims, No Drawings

HYDROLYSIS OF ALKYLENE CARBONATES TO AKLYLENE GLYCOLS

This application is a continuation of application Ser. No. 100,223, filed Dec. 4, 1979, now abandoned, which is a continuation of Ser. No. 863,351, filed Dec. 22, 1977, now abandoned.

This invention is concerned with the production of an alkylene glycol by the hydrolysis of the corresponding alkylene carbonate. More particular, this invention relates to a process which achieves better rates of reaction and exceptional efficiency of conversion by hydrolysis of alkylene carbonates to the glycols. The process of this invention can be utilized to produce ethylene glycol which when catalyst and water are removed can meet the stringent requirements of Polyester Fiber grade, see companion patent application Ser. No. 863,354, filed Dec. 22, 1977, now U.S. Pat. No. 4,314,945, for a definition thereof.

The hydrolysis of alkylene carbonates to the corresponding alkylene glycols is known. For example, Peppel, *Industrial and Engineering Chemistry*, Volume 50, Number 5 (May, 1958), pages 767–770, states at page 769, that ethylene carbonate and propylene carbonate may be hydrolyzed by water, utilizing one molar aqueous solution at 100° C., with or without catalyst. The particular catalysts mentioned are sodium carbonate and sulphuric acid. According to Peppel, supra, "Hydrolysis of ethylene carbonate is accelerated greatly by bases and to a much lesser extent by acids." Levin et al., U.S. Pat. No. 3,629,343, patented Dec. 21, 1971, describe a process which involves the reaction of ethylene oxide with water and carbon dioxide at temperatures of 80°–220° C. to eventually produce ethylene glycol. The authors state that one of the possible intermediate steps is the formation of ethylene carbonate which is hydrolyzed to ethylene glycol. The reaction is carried out with a catalyst mixture comprising the halo salts of tetraalkylammonium compounds or polyhaloacid salts of amines, and the second catalyst which is employed is a compound having basic character such as "carbonates, bicarbonates or hydroxides of alkali metals. " The examples of the patent specifically illustrate sodium bicarbonate, potassium bicarbonate, sodium carbonate, sodium bicarbonate and sodium hydroxide. Pohoryles et al., *Journal of the Chemical Society*, pages 3082–3086 (1960), describe the hydrolysis of substituted cyclic, alpha, beta and alpha, gamma-carbonates using potassium carbonate. In this work, the authors employed at least a stoichiometric amount of the potassium carbonate to the alkylene carbonate being hydrolyzed. At page 3083, the authors made the following statement:

"Alkaline hydrolysis of the cyclic alpha, beta and alpha, gamma-carbonates was too rapid even at 0° in very dilute solutions of alkali hydroxides, but it was slow enough in potassium carbonate solution for convenient measurement."

Thus, potassium carbonate was not a catalyst of choice but used only as a buffer, producing a mild alkaline solution, to study the mechanisms of alkaline induced ester hydrolysis, in dilute solutions.

There is described herein the surprising development that more rapid reaction can be effected in the hydrolysis of alkylene carbonates employing catalytic amounts of potassium carbonate and $CO_2$ than is obtainable with any other alkali bicarbonates, carbonates or hydroxides. Indeed, more rapid hydrolysis can be effected from the use of potassium carbonate and $CO_2$ than can be achieved from the use of potassium carbonate. Thus, quite unexpectedly, this particular compound has been found under select conditions of operation to achieve results which heretofore would have not been predictable.

Sarel et al., *Journal of the Chemical Society*, pages 3079–3082 (1960), indicate on page 3082 the complexity of the reactions involved in the hydrolysis of an alkylene carbonate such as ethylene carbonate to produce the ultimate product, i.e., ethylene glycol. According to those authors, there are several intermediate products produced before one obtains the ultimate ethylene glycol product. In describing the process of this invention, speculation will not be made with respect to the various intermediates which can or cannot be formed. The process of this invention so rapidly produces the ultimate glycol that recognition of intermediates which might be formed is extremely difficult, if not impossible by present state of the art.

The catalyst employed in the process of this invention may be any potassium compound which when incorporated into protic medium under carbon dioxide pressure produces potassium carbonate, either as the ionic form or potassium bicarbonate form.

Thus, one may introduce potassium hydroxide to such a medium and convert it under $CO_2$ pressure to the equivalent of the catalyst that one would derive from the use of potassium carbonate only. However, this is not considered an effective method by which to obtain the catalytic specie.

The amount of the catalyst that one employs in practicing the process of this invention contributes significantly to the rate of the reaction. The amount of the catalyst, based on the weight of alkylene carbonate, can be as little as 0.03 weight percent to as much as 10 weight percent. In making these calculations the catalyst is considered to be potassium carbonate. The preferred amount of catalyst is about 0.1 to about 5.0 weight percent. To achieve the greatest catalytic effect for the amount of catalyst employed, the most preferred amount of the catalyst is 0.25 weight percent to about 1.5 weight percent, based on the weight of alkylene carbonate.

In carrying out the process, the minimum temperature to employ is 85° C. The temperature may be as high as 500° C. and when temperatures that high are employed it is desirable to make adjustments in the amount of catalyst employed; the smaller amount of catalyst compensating for the increased temperature. In a preferred operation of the process of this invention it is desirable to keep the temperature of the reaction between about 100° and about 300° C. In the most practical utilization of the process of this invention, the preferred temperature is between about 120° and 200° C. When utilizing a back-mix reactor, it is possible that the rate of the reaction can be so great that one should be very careful in selecting not only the amount of catalyst and the proportion of reactant but also the temperature employed. A maximum temperature in the range of 170° to 200° C. is quite easily achieved, provided such care is given.

The reaction is also carried out under pressure utilizing a carbon dioxide pressure of greater than 80 psig. There is no apparent maximum pressure that limits the employment of this invention. However, there are practical considerations which one can employ in determining a maximum pressure. In terms of economic benefits it would be desirable not to employ a pressure exceeding 2000 psig. Most desirably the maximum pressure does not exceed about 1000 psig. In selecting pressure one has to take into consideration the type of equipment which is available and being utilized. Should this process be carried out in available equipment which is capable of taking very high pressure and there appears to be under any conditions of the reaction sufficient reason for doing so because of the fact that higher pressure carbon dioxide is available, then of course the disadvantages that would be attributable to the use of such higher pressures will be mitigated.

Another factor to be considered in carrying out the process of this invention is the amount of water which is provided in the feed to the reactor in which the reaction is either effected, in a batch or continuous operation.

The initial mole ratio of water to alkylene carbonate which is employed in the hydrolysis reaction, that is, the amount of water which is combined with the alkylene carbonate in the reaction zone in order to effect hydrolysis, should be at least one mole of water per mole of alkylene carbonate. However, from a practical standpoint, in order to achieve the kind of performance characterized for the process of this invention, one should employ at least about 1.2 moles of water to about 10 moles of water for each mole of alkylene carbonate. The most preferred ratio is about 1.5 to 2.5:1. For example, when that mole ratio is below about 1.2, in the hydrolysis of ethylene carbonate, it becomes very difficult to produce Polyester Grade ethylene glycol. In addition, mole ratios below 1.2 make it difficult to minimize the production of diethylene glycol or dispropylene glycol.

The process of this invention can be operated in the presence of a solvent which serves the purpose of, at the most, diluting the reaction mixture. Any liquid at the reaction temperature which is miscible with the alkylene carbonate and the glycol product can be, to the extent that it continues to be miscible in the system, a solvent provided that it is not reactive with either the alkylene carbonate reactant, the glycol produced or the potassium catalyst employed. Such chemicals as carboxylic acids, phenols, aldehydes, alkylene oxides, other than ethers of the non-vicinyl type, may not be employed as solvents in the practice of this invention. Alkylene carbonates and the resulting alkylene glycol are very good solvents. It is desirable that the alkylene carbonate employed is the same as the alkylene carbonate reactant and that the glycol employed as a solvent is the same as the product glycol being produced. The only effect that one obtains from the use of such solvents is that they reduce, to the extent of dilution, the rate of reaction. However, they do not adversely affect the percent conversion or the efficiency of the reaction. They are useful for the purpose of controlling reaction temperature and rate; and assist in recycle systems when this is carried out in a continuous fashion.

The process of this invention may be carried out as a batch reaction or as a continuous process. The batch reactions may be carried out in pressure resistant vessels suitably constructed to withstand the pressures of this reaction.

The process, as stated, may be employed in a conventional autoclave or can be effected in a glassware type of equipment when operated at moderate pressures. It may also be employed in a plug-flow reactor utilizing conventional procedures to effect the process continuously. Solvent may be recycled and catalyst may be recovered. The process is very advantageously employed by concentrating the catalyst over a vacuum evaporator and recycling it to the reaction.

The reaction may be carried out for very short periods of time in terms of fractions of a second and if desired may be carried out over reaction periods amounting to hours. These conditions of reaction are governed by the amounts of solvent and catalyst employed, the pressures and temperatures employed, and like considerations. A most favorable utilization of this invention may be found in copending application Ser. No. 863,352, filed Dec. 22, 1977, now U.S. Pat. No. 4,117,250.

The following examples depict various modes in the practice of this invention including those modes which are considered to be best for the practice of this invention. It is not intended that this invention shall be limited by the examples.

EXAMPLE 1

A stirred 5-gallon stainless steel autoclave capable of withstanding pressures of up to 5000 psig with provisions for batchwise charging of reactants, a continuous gas discharge line and a drain point for collection of liquid product at the completion of each run, was assembled. The contents of the autoclave were mixed with a dispersimax-type agitator 5 inches in diameter comprised of 6 flat blades. The autoclave was supplied with an internal steam coil and external electric heaters. Cooling was accomplished by adding water to the internal coil through a series of valves.

The reactor was charged with a mixture of ethylene carbonate (4000 grams, 45.45 moles), water (1536 grams, 90.0 moles) and monoethylene glycol (285 grams, 4.6 moles) and heated by use of 200 psig of steam in the internal reactor coils and external electrical heaters. When the desired reaction temperature of 150° C. was reached, $CO_2$ was sparged into the reactor until an operating pressure of 500 psig was attained. At this point, the catalyst (48 grams of 0.35 moles, $K_2CO_3$ dissolved in 100 grams of water) was charged to the reactor. The feed mole ratio of water to ethylene glycol was 2.0; the feed of $K_2CO_3$ concentration (weight percent based on ethylene carbonate feed) was 1.2; the feed monoethylene glycol (weight percent based on total feed) was 5.0.

During the reaction, the mixture was agitated at 1000 rpm. Temperature was controlled via a single thermocouple centered in the liquid phase and pressure control was achieved by a backpressure regulator on the discharge line. A vapor phase, consisting principally of $CO_2$ and water was continuously discharged during reaction. A record of the time elapsed during the discharge of each 0.25 cubic foot of vapor was made by linking a strip chart recorder to a photocell which in turn monitored a dry test meter equipped with a metal cross on the indicator dial. This cross interrupted the light to the photocell every quarter revolution of the meter dial. Off-gas rate was corrected to standard conditions by use of continuous temperature and pressure measurements at the outlet of the gas meter.

Upon completion of a run, the reactor contents were discharged and weighed to determine efficiencies. Rates of reaction were based on the total amount of off-gas accumulated as a function of time. The time to reach percent conversion at 150° C., 500 psig, 2.0 feed mole ratio of water to ethylene carbonate, 1.2 weight percent of $K_2CO_3$ and 5.0 weight percent of monoethylene glycol was 1.3, 4.0, 6.5, 11.6, and 14.4 minutes respectively at 20, 50, 70, 90 and 95 percent conversion, respectively, of ethylene carbonate to monoethylene glycol.

EXAMPLES 2 TO 16

Example 1 was exactly repeated except that reaction temperature and pressure; feed mole ratio of water to ethylene glycol (A); feed $K_2CO_3$ concentration, weight percent based on ethylene glycol feed (B); feed monoethylene glycol concentration, weight percent based on total feed (C); and the time in minutes to reach the percent conversion (20, 50, 70, 90 and 95) at the aforesaid conditions (based on $CO_2$ evolution) are as set forth in TABLE I.

discharge of each 0.5 liter of vapor was made by linking a recorder to the above mentioned modified telometer switch which in turn monitored a wet test meter. Upon completion of a run, the reaction contents were discharged and weighed to determine efficiencies. Rates of reaction were based on the total amount of off-gas accumulated as a function of time. The feed mole ratio of water to ethylene carbonate was 2.0; the feed of $K_2CO_3$ concentration (weight percent based on ethylene carbonate feed) was 0.60. The time to reach percent conversion at 130° C., 108 psig, 2.0 feed mole ratio of water to ethylene carbonate, 0.6 weight percent of $K_2CO_3$ was 11.9, 31.8, 54.0, 92.0 and 105 minutes at 20, 50, 70, 90, 95 percent conversions of ethylene carbonate to monoethylene glycol, respectively.

TABLE I

Rate of Conversion of Ethylene Carbonate to Monoethylene Glycol as a Function of the Reaction Parameters

| Example | Temp. (°C.) | Pressure (psig) | A | B | C | *$t_{20\%}$ | *$t_{50\%}$ | *$t_{70\%}$ | *$t_{90\%}$ | *$t_{95\%}$ |
|---|---|---|---|---|---|---|---|---|---|---|
| 2 | 160 | 1510 | 2.5 | 0.6 | 0.0 | 3.2 | 10.0 | 16.6 | 28.9 | 35.9 |
| 3 | 150 | 510 | 2.5 | 0.6 | 8.9 | 3.3 | 8.7 | 13.5 | 22.2 | 26.9 |
| 4 | 150 | 510 | 2.5 | 1.2 | 0.0 | 1.3 | 3.8 | 6.2 | 10.4 | 12.6 |
| 5 | 145 | 1000 | 2.0 | 0.9 | 5.0 | 4.0 | 15.3 | 26.8 | 49.7 | 63.1 |
| 6 | 130 | 150 | 2.5 | 0.6 | 9.6 | 3.6 | 10.3 | 16.3 | 26.9 | 32.5 |
| 7 | 130 | 350 | 2.5 | 0.6 | 0.0 | 7.3 | 19.0 | 31.8 | 59.3 | 76.6 |
| 8 | 160 | 1400 | 2.5 | 1.2 | 10.1 | 1.8 | 5.3 | 8.7 | 15.4 | 19.1 |
| 9 | 160 | 1300 | 2.5 | 1.2 | 10.1 | 1.7 | 5.2 | 8.4 | 14.5 | 17.9 |
| 10 | 160 | 1200 | 2.5 | 1.2 | 10.1 | 1.6 | 4.3 | 6.9 | 12.0 | 14.9 |
| 11 | 130 | 500 | 2.5 | 1.2 | 0.0 | 4.2 | 12.9 | 21.6 | 37.6 | 47.0 |
| 12 | 160 | 510 | 1.5 | 0.6 | 0.0 | 1.1 | 3.2 | 5.6 | 10.6 | 13.7 |
| 13 | 160 | 520 | 2.5 | 1.2 | 0.0 | 1.1 | 2.1 | 3.3 | 5.8 | 7.4 |
| 14 | 130 | 500 | 1.5 | 1.2 | 0.0 | 4.1 | 15.2 | 27.2 | 53.2 | 69.5 |
| 15 | 130 | 500 | 1.5 | 0.6 | 10.1 | 12.0 | 43.0 | 76.8 | 149.5 | 195.4 |
| 16 | 130 | 500 | 2.5 | 0.6 | 8.9 | 10.9 | 34.7 | 58.0 | 101.9 | 126.5 |

*$t_i$ in minutes to reach i % conversion of ethylene carbonate to monoethylene glycol

EXAMPLE 17

A 120 cc Parr bomb equipped with a sample line, thermocouple and a magnetic stirring bar was assembled. $CO_2$ evolution was monitored with a wet test meter modified by adding five metallic contact points to the face of the meter and connecting them to a telemeter switch, to produce a line on a variable speed recorder every 0.5 liters. The Parr bomb was heated with an electric heater and pressure was regulated using a Nupre adjustable in-line relief valve.

The Parr bomb was charged with ethylene carbonate (88.0 grams, 1.0 mole), water (36.0 grams, 2.0 moles) and $K_2CO_3$ catalyst (0.5 gram, 0.57 weight percent based on ethylene carbonate). The system was pressurized with $CO_2$ until 3.0 liters had passed through the wet test meter. At this point, the flow was turned off and the mixture allowed to stand until no further $CO_2$ absorption was observed. The system as brought to a temperature of 130° C. and a pressure of 108 psig and stirring was begun. A vapor phase consisting principally of $CO_2$ and water was continuously discharged during the reaction. A record of the time elapsed during

EXAMPLES 18 TO 20

Example 17 was exactly repeated except that reaction temperature and pressure; feed mole ratio of water to ethylene carbonate (A); feed $K_2CO_3$ concentration, weight percent was based on ethylene carbonate feed (B); and the time in minutes to reach the percent conversion (20, 50, 70, 90, and 95) at the aforesaid conditions (based on $CO_2$ evolution) are set forth in TABLE II.

EXAMPLES 21 TO 23

Example 17 was exactly repeated except that monoethylene glycol was charged with the ethylene carbonate, water and $K_2CO_3$ catalyst. The reaction temperature and pressure; feed mole ratio of water to ethylene carbonate (A); feed $K_2CO_3$ concentration, weight percent based on ethylene carbonate feed (B); monoethylene glycol concentration, weight percent based on total feed (C); and the time in minutes to reach the percent conversion (20, 50, 70, 90, and 95) at the aforesaid conditions (based on $CO_2$ evolution) are set forth in TABLE II.

TABLE II

Rate of Conversion of Ethylene Carbonate to Monoethylene Glycol as a Function of the Reaction Parameters

| Example | Temp. (°C.) | Pressure (psig) | A | B | C | *$t_{20\%}$ | *$t_{50\%}$ | *$t_{70\%}$ | *$t_{90\%}$ | *$t_{95\%}$ |
|---|---|---|---|---|---|---|---|---|---|---|
| 18 | 106 | 83 | 2.0 | 1.3 | — | 23.6 | 69.0 | 110.0 | 185.2 | 230.0 |
| 19 | 105 | 102 | 4.0 | 0.6 | — | 38.0 | 104.7 | 164.0 | 260.0 | 298.0 |
| 20 | 107 | 102 | 2.0 | 0.3 | — | 90.0 | 250.0 | 405.0 | 660.0 | 780.0 |
| 21 | 104 | 107 | 2.0 | 1.7 | 1.0 | 25.4 | 68.0 | 100.0 | 160.0 | 197.0 |
| 22 | 104 | 103 | 3.0 | 0.6 | 30.3 | 56.0 | 148.0 | 258.0 | 422.0 | 490.0 |

TABLE II-continued
Rate of Conversion of Ethylene Carbonate to Monoethylene Glycol as a Function of the Reaction Parameters

| Example | Temp. (°C.) | Pressure (psig) | A | B | C | *$t_{20\%}$ | *$t_{50\%}$ | *$t_{70\%}$ | *$t_{90\%}$ | *$t_{95\%}$ |
|---|---|---|---|---|---|---|---|---|---|---|
| 23 | 104 | 110 | 4.4 | 2.4 | 54.8 | 26.0 | 70.0 | 107.0 | 172.0 | 205.0 |

*$t_i$ in minutes to reach i % conversion of ethylene carbonate to monoethylene glycol

What is claimed is:

1. The process of making glycols of the formula

HOCHRCH$_2$OH which comprises hydrolyzing in a homogeneous liquid phase mixture, an alkylene carbonate of the formula

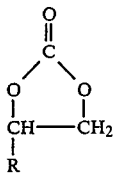

in which R is either hydrogen or methyl with an amount of water which is in excess of stoichiometry according to the equation

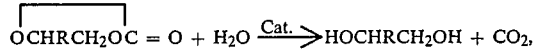

$$\overline{OCHRCH_2OC} = O + H_2O \xrightarrow{Cat.} HOCHRCH_2OH + CO_2,$$

employing a catalytic amount of potassium carbonate, and maintaining the mixture under a CO$_2$ pressure of at least 80 psig at a temperature of between about 85° C. and 500° C.

2. The process of claim 1, wherein the alkylene carbonate is ethylene carbonate.

3. The process of claim 1, wherein the alkylene carbonate is propylene carbonate.

4. The process of claim 1, wherein the amount of K$_2$CO$_3$ catalyst is about 0.1 to about 5.0 weight percent based on the amount of alkylene carbonate.

5. The process of claim 4, wherein the amount of catalyst is 0.25 to about 1.5 weight percent.

6. The process of claim 1, wherein the temperature is between about 100° C. to about 300° C.

7. The process of claim 6, wherein the temperature is between about 120° to about 200° C.

8. The process of claim 1, wherein the pressure is between about 80 to about 2000 psig.

9. The process of claim 1, wherein the amount of water is in the ratio of at least about 1.2 to about 10 moles of water for each mole of alkylene carbonate.

10. The process of claim 9, wherein the mole ratio of water to alkylene carbonate is about 1.5 to 2.5:1.

11. The process of claim 1 wherein the process is operated in the presence of a solvent.

12. The process of claim 11, wherein the solvent is an alkylene carbonate.

13. The process of claim 12, wherein the alkylene carbonate is ethylene carbonate.

14. The process of claim 11, wherein the solvent is alkylene glycol.

15. The process of claim 14, wherein the alkylene glycol is ethylene glycol.

16. The process of claim 1, wherein the glycol product is ethylene glycol.

17. The process of claim 1, wherein the glycol product is propylene glycol.

* * * * *